United States Patent
Robins et al.

[11] Patent Number: 5,942,694
[45] Date of Patent: Aug. 24, 1999

[54] PRESSURE DETECTOR FOR CHEMICAL ANALYZERS

[75] Inventors: William M. Robins, La Habra; Donald P. Labriola, II, La Verne, both of Calif.; John W. Strom, Indiana, Pa.

[73] Assignee: Beckman Instruments, Inc., Fullerton, Calif.

[21] Appl. No.: 08/748,135

[22] Filed: Nov. 12, 1996

[51] Int. Cl.$^6$ ...................................................... G01L 7/00
[52] U.S. Cl. .............................. 73/756; 73/700; 73/714; 73/715
[58] Field of Search ........................... 73/864.34, 864.11, 73/863.01, 863.03, 864.21, 864.81, 700, 715, 716, 723, 714, 756; 340/608, 625; 417/38; 422/112; 216/741

[56] References Cited

U.S. PATENT DOCUMENTS

| | | |
|---|---|---|
| 4,399,711 | 8/1983 | Klein . |
| 4,419,903 | 12/1983 | Jackson . |
| 4,893,515 | 1/1990 | Uchida .................................... 73/864.3 |
| 4,965,049 | 10/1990 | Lillig et al. . |
| 5,393,434 | 2/1995 | Hutchins et al. ........................ 210/656 |
| 5,503,036 | 4/1996 | Nguyen et al. . |

*Primary Examiner*—Ponnathapura Achutamurthy
*Assistant Examiner*—Joseph W. Ricigliano
*Attorney, Agent, or Firm*—William H. May; P. R. Harder; Sheldon & Mak

[57] ABSTRACT

An apparatus is provided for detecting the pressure of a fluid. The device includes a device for detecting the pressure of a fluid comprising (a) a housing; (b) a first conduit disposed within the housing, having an open inlet end, and an outlet end; (c) a second conduit disposed within the housing having an inlet end and an open outlet end; and (d) a pressure detector disposed within the housing in abutment with the outlet end of the first conduit and the inlet end of the second conduit, such that the pressure detector is in direct operative contact with a fluid flowing within the first and second conduits. Typically, the pressure detector is a pressure transducer. Preferably, the pressure transducer is located within the body, such that the first conduit is disposed at an angle with respect to the pressure sensitive surface of the transducer, the angle being between about 50° and about 75°, most preferably between about 65° and about 70°. It is also preferable that the fluid is a degassed liquid such as degassed water.

8 Claims, 9 Drawing Sheets

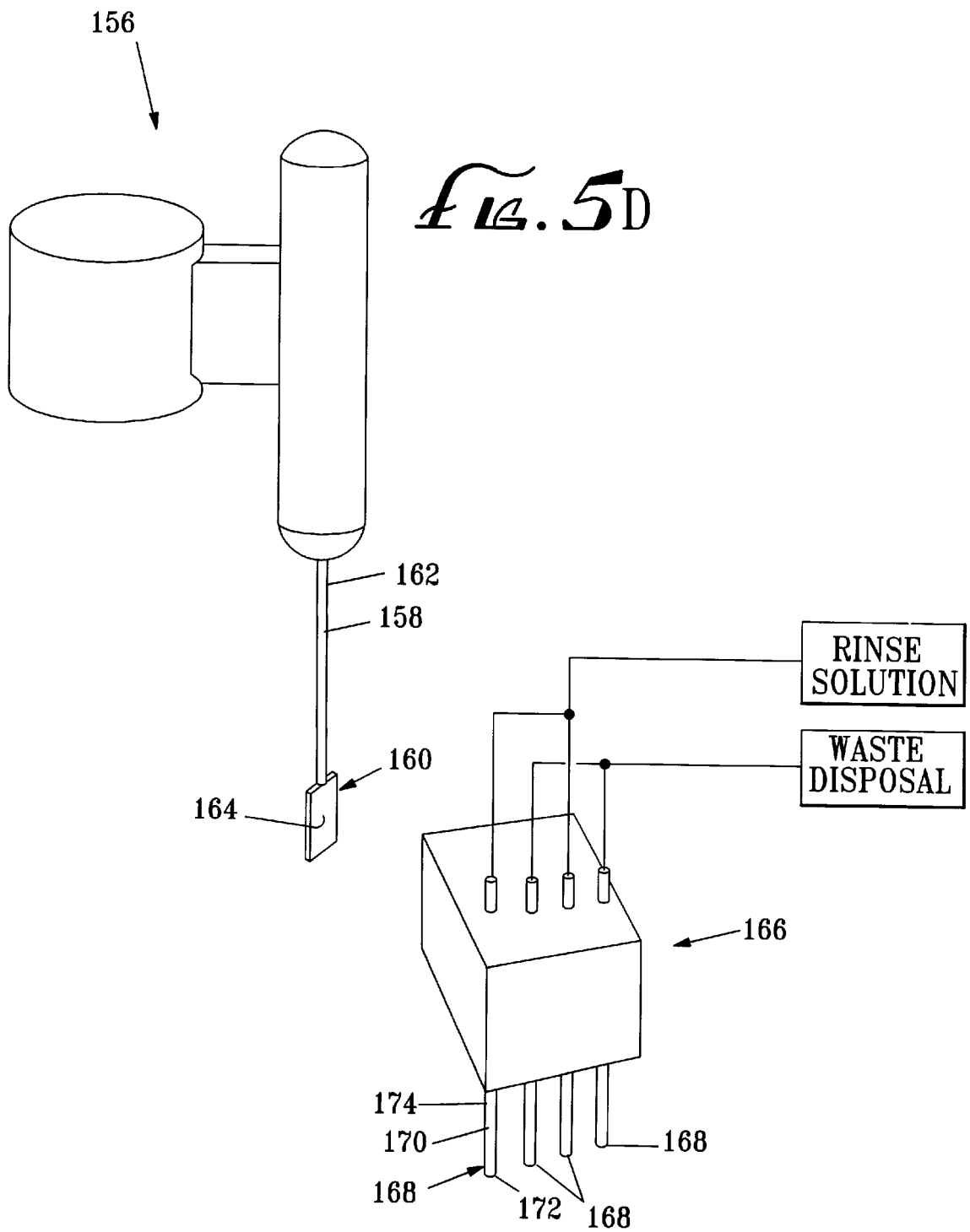

PRESSURE DETECTOR FOR CHEMICAL ANALYZERS

FIELD OF THE INVENTION

This invention generally relates to the field of automated clinical chemical analyzers, and specifically to high throughput automated chemical analyzers having automated extraction and discharge probes.

BACKGROUND OF THE INVENTION

A number of different automated clinical chemical analyzers are known in the art. Such analyzers range from simple, largely manually operated instruments to highly complex, nearly fully automated instruments. Each analyzer has its own particular performance characteristics related to the number ("menu") of different tests that the analyzer can perform and the number of samples that can be processed in a given period of time ("throughput").

Large scale, highly complex analyzers useful in large hospitals and clinical laboratories have been developed which have both a large menu of tests which the instrument can perform and a high throughput. Such an analyzer is described in U.S. Pat. No. 4,965,049 issued to Lillig et al. which is incorporated herein by reference in its entirety.

Most such large scale, highly complex analyzers employ liquid extraction and discharge equipment comprising hollow open-ended extraction/discharge probes operatively connected to sources of vacuum and pressure. Such probes can be conveniently used to extract a predetermined quantity of liquid from one container within the analyzer and deposit that liquid into another container within the analyzer. In a typical configuration, the sources of vacuum and pressure are syringe-type pumps which alternatively push or pull a carrier liquid toward the probes or away from the probes.

In such configurations, problems arise within the analyzers when solid materials, such as dried chemicals or foreign materials obstruct the lines carrying the carrier liquid to the extraction/discharge probes. Such obstructions affect the extraction and discharge functions of the probe and can therefore seriously affect the efficiency of the analyzer and/or the quality of the analyses performed by the analyzer. Accordingly, such obstructions need to be identified immediately when they occur.

Several obstruction detection methods have been proposed. One of the most sophisticated uses a transducer to continuously monitor pressure within the carrier liquid lines. Unfortunately, even this sophisticated detection method has not been fully satisfactory. Specifically, the transducers have not been able to monitor pressures within the carrier liquid lines with sufficient accuracy. This is because prior art configurations operatively connect the transducer to the carrier liquid lines using an intermediary conduit which may be filled with air, carrier liquid or some other non-flowing fluid. Such intermediary conduits delay and dampen pressure transmissions from the flowing carrier liquids to the transducer. Also, the intermediary conduits tend to become clogged with foreign material.

Apart from these problems with the intermediary conduits, dissolved gases within prior art configurations tend to also delay and dampen pressure transmissions from the flowing carrier liquid to the transducer.

Accordingly, there is a need for an obstruction detection apparatus which can efficiently detect obstructions within the pressure/vacuum lines of automated chemical analyzers with a high degree of accuracy.

SUMMARY OF THE INVENTION

The invention satisfies these needs. The invention is a device for detecting the pressure of a fluid, the device comprising (a) a housing; (b) a first conduit disposed within the housing, the first conduit having an open inlet end and an open outlet end; (c) a second conduit disposed within the housing, the second conduit having an inlet end in fluid tight communication with the outlet end of the first conduit and an open outlet end; and (d) a pressure detector disposed within the housing in abutment with the outlet end of the first conduit and with the inlet end of the second conduit such that the pressure detector is in direct operative contact with a fluid flowing within the first and second conduits. By "direct operative contact" it is meant that the pressure detector contacts the fluid flowing within the conduits without use of any intermediary nonflowing liquid-filled conduit.

In a typical embodiment, the pressure detector is a pressure transducer. Preferably, the pressure sensitive surface of the transducer is disposed within the body tangent to a transducer plane and the first conduit is linear and disposed at an angle within respect to the transducer plane of between about 50° and about 75°, most preferably between about 65° and about 75°.

It is also preferable that the carrier fluid is a degassed liquid, such as water degassed under a vacuum of at least about 20 inches of mercury.

The invention is useful in a combination for extracting a liquid from a first container and depositing that liquid into a second container. Such a combination comprises (a) a movable hollow probe having an open first end and an second end; (b) a fluid tight first conduit moiety having a first end and a second end, the first end of the first conduit moiety being attached in fluid tight communication to the second end of the probe; (c) a fluid tight second conduit moiety having a first end and a second end; (d) a pump disposed in fluid tight communication with the second end of the second conduit moiety, the pump being constructed so that it can alternatively apply either a positive pressure or a negative pressure on the second end of the second conduit moiety; and (e) a pressure detecting device having: (i) a housing; (ii) a first conduit disposed within the housing, the first conduit having an open inlet end and an open outlet end; (iii) a second conduit disposed within the housing, the second conduit having an inlet end in fluid tight communication with the outlet end of the first conduit and an open outlet end; and (iv) a pressure detector disposed within the housing in abutment with the outlet end of the first conduit and with the inlet end of the second conduit such that the pressure detector is in direct operative contact with a fluid flowing within the first and second conduits.

Such a combination, in turn, is useful in an automated liquid chemical analysis device comprising (a) a body; (b) a sample station disposed within the body, the sample station being sized and dimensioned to retain a plurality of sample containers; (c) a reagent station disposed within the body, the reagent station being sized and dimensioned to retain a plurality of reagent containers; and (d) an analyzing station disposed within the body, the analyzing station comprising: (1) a reaction container and (2) an analyzer for analyzing liquids disposed within the reaction container.

The invention provides significant improvements over the prior art by reducing maintenance costs and operating expense, while increasing throughput accuracy and reliability.

DESCRIPTION OF THE DRAWINGS

These and other features, aspects and advantages of the present invention will become better understood with reference to the following description, appended claims and accompanying drawings where:

FIG. 5D is a perspective view of a cuvette stirring rod assembly;

FIG. 5E is a perspective view of a cuvette wash station;

DETAILED DESCRIPTION

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Figure 1:
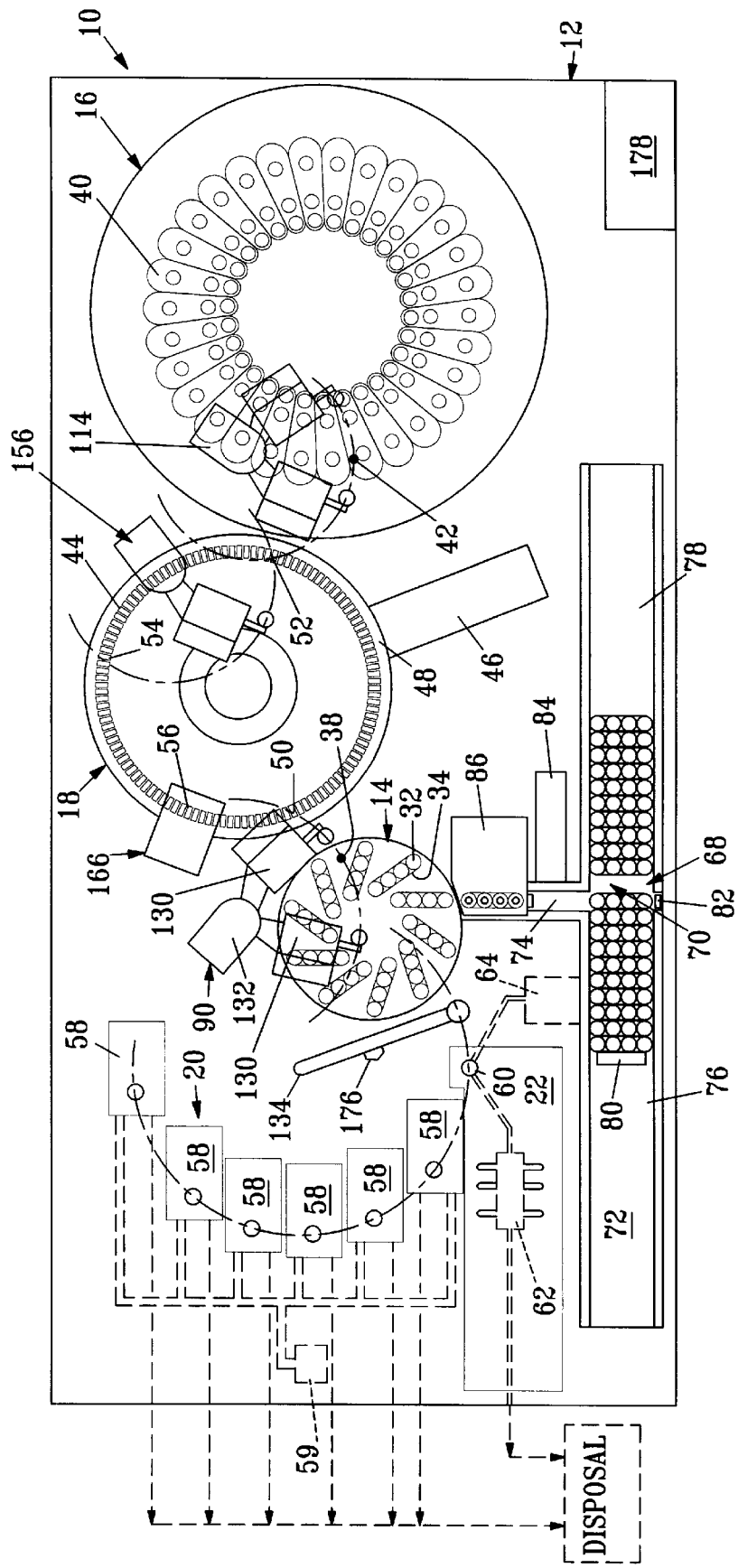
FIG. 1 is a schematic plan view of an automated analyzing machine having features of the invention.
Figure 2:
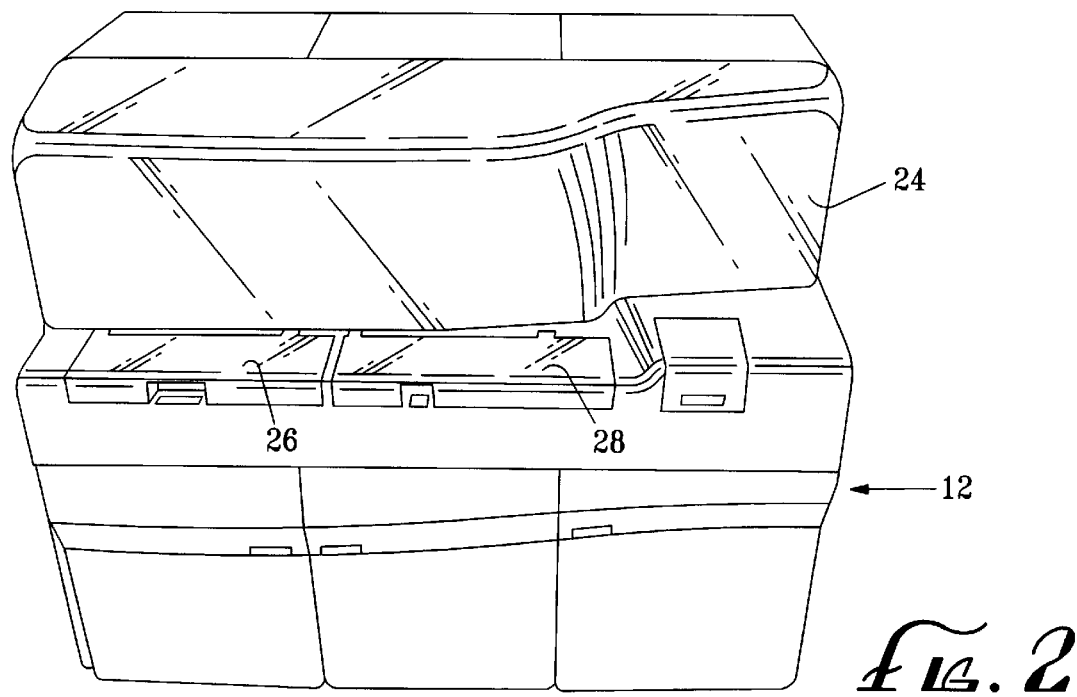
FIG. 2 is a front view of an automated analyzing machine having features of the invention with its canopy closed.
Figure 3:
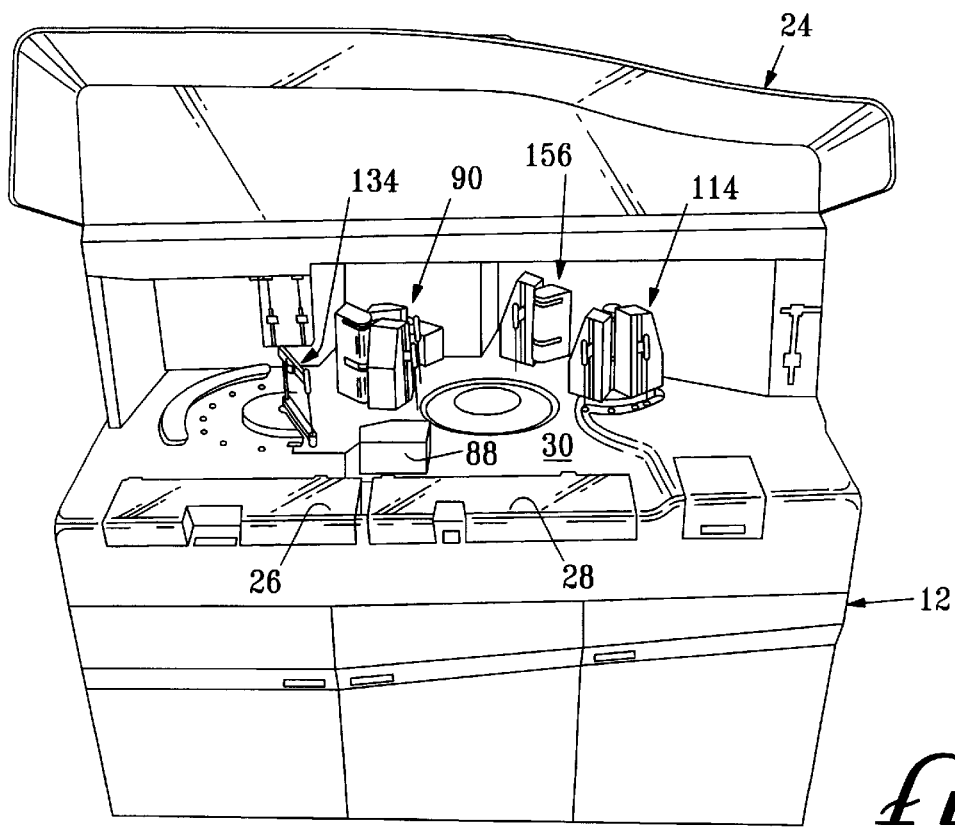
FIG. 3 is another front view of the automated analyzing machine of FIG. 2 shown with its canopy open.

FIGS. 1–3 show an automated analyzing machine 10 having features of the invention. The machine 10 comprises a body 12, a sample station 14, a reagent station 16, a random access analyzing station 18, a reaction cup analyzing station 20 and an ion selective electrode analyzing station 22.

The body 12 is typically a cabinet providing a housing for the various operative components. The body 12 is typically made from a lightweight metal such as a lightweight sheet steel. The embodiment shown in FIGS. 2 and 3 includes a hinged primary canopy 24. FIG. 2 shows the analyzing machine 10 with the primary canopy 24 closed. FIG. 2 shows the machine with the primary canopy 24 open.

FIGS. 2 and 3 also illustrate how a typical analyzing machine 10 of the invention can have an on-load tray cover 26, an off-load tray cover 28 and one or more operator area covers 30 covering the sample station 14, the reagent station 16, the random access analyzing station 18, the reaction cup analyzing station 20 and the ion selective electrode analyzing station 22.

Figure 4A:
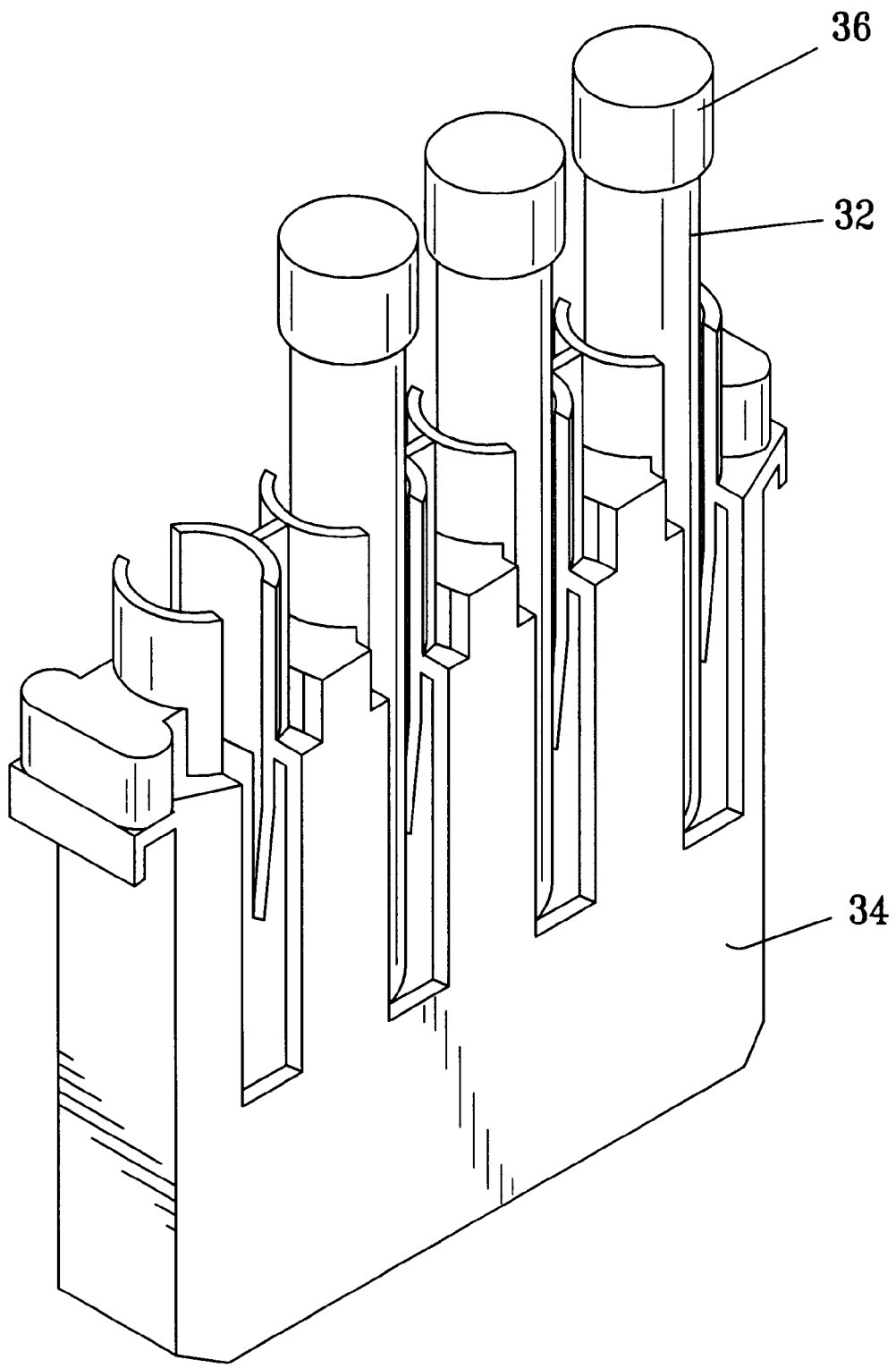
FIG. 4A is a perspective of a sample container rack useful in the invention.

The sample station 14 is sized and dimensioned to retain a plurality of sample containers 32. In the embodiment shown in FIGS. 1–3, the sample station 14 is a revolving circular carousel capable of retaining 40 sample containers 32 disposed in 10 sample container racks 34. In a typical embodiment, each sample container 32 is a generally upright container having a container cap 36 of thin rubber or like material. A sample container rack 34 containing four sample containers 32 useful in the invention is shown in FIG. 4A. The sample station 14 is moveable by a rotating motor (not shown) such that each sample container 32 can be alternatively positioned under and moved away from at least one sample extraction site 38.

The reagent station 16 is sized and dimensioned to retain a plurality of reagent containers 40. Each reagent container 40 contains one or more compartments for retaining one or more different reagents useful in the analysis chemistry performed by the analyzing machine 10. Also, it is preferable to predilute the reagent to minimize reagent usage and dilution step delays. A preferred reagent container 40 design has three individual compartments and is described in detail in U.S. Pat. Nos. 4,970,053 and 5,075,082, which are both incorporated herein by this reference in their entireties.

Preferably, the reagent station 16 is refrigerated, such as to a temperature of about 4° C., to preserve reagent life and minimize evaporation.

In the embodiment shown in FIGS. 1–3, the reagent station 16 is a revolving circular carousel. The reagent station 16 is movable by a rotating motor (not shown) such that each reagent container 40 can be alternatively positioned under and moved away from at least one reagent extraction site 42.

Preferably, the reagent station 16 also includes a bar code reader (not shown) which reads bar-coded information printed on the reagent containers 40 and/or disposed on the reagent carousel. Such information can be transmitted to a computerized controller to assist in operation of the analyzing machine 10.

Figure 4B:
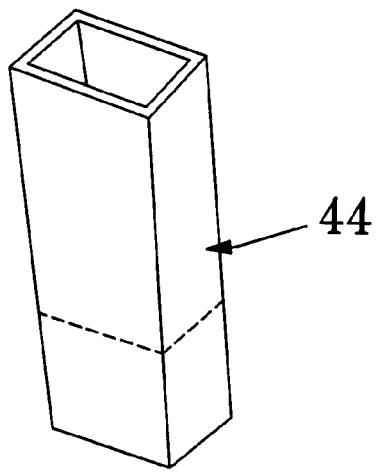
FIG. 4B is a perspective view of a reaction cuvette useful in the invention.
Figure 4C:
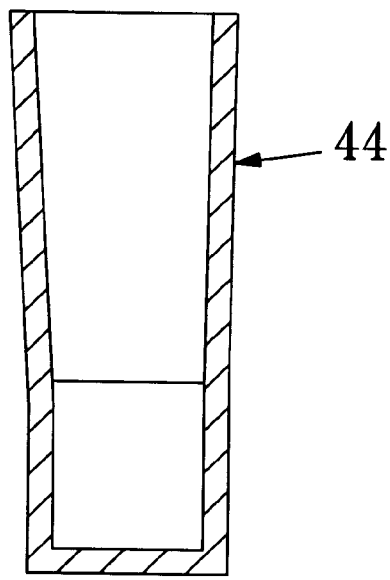
FIG. 4C is a cross-sectional side view of the reaction cuvette shown in FIG. 4B.

The random access analyzing station 18 is sized and dimensioned to retain a plurality of reaction cuvettes 44 as illustrated in FIGS. 4B and 4C. In the embodiment shown in FIGS. 1–3, the random access analyzing station 18 is a revolving circular carousel capable of retaining in excess of 100 cuvettes 44. Each cuvette 44 is a small open top reaction container having at least two opposed transparent sides through which a beam of light can be directed.

The random access analyzing station 18 further comprises random access analyzing station analyzer 46, such as a nephelometer and/or photometer disposed proximate to a random access analyzing station analyzing site 48 for determining at least one parameter of a sample disposed within the cuvettes 44.

The random access analyzing station 18 is movable by a rotating motor (not shown) such that each cuvette 44 can be alternatively positioned under and moved away from at least one cuvette sample deposit site 50, at least one cuvette reagent deposit site 52, at least one cuvette mixing site 54, at least one cuvette washing site 56 and the one random access analyzing station analyzing site 48.

The reaction cup analyzing station 20 comprises at least one reaction cup module 58. In the embodiment shown in FIG. 1, the reaction cup analyzing station 20 comprises six reaction cup modules 58. Each reaction cup module 58 can be used to measure high volume analyses such as analyses for sodium, potassium, glucose, creatinine and blood urea nitrogen.

Figure 6:
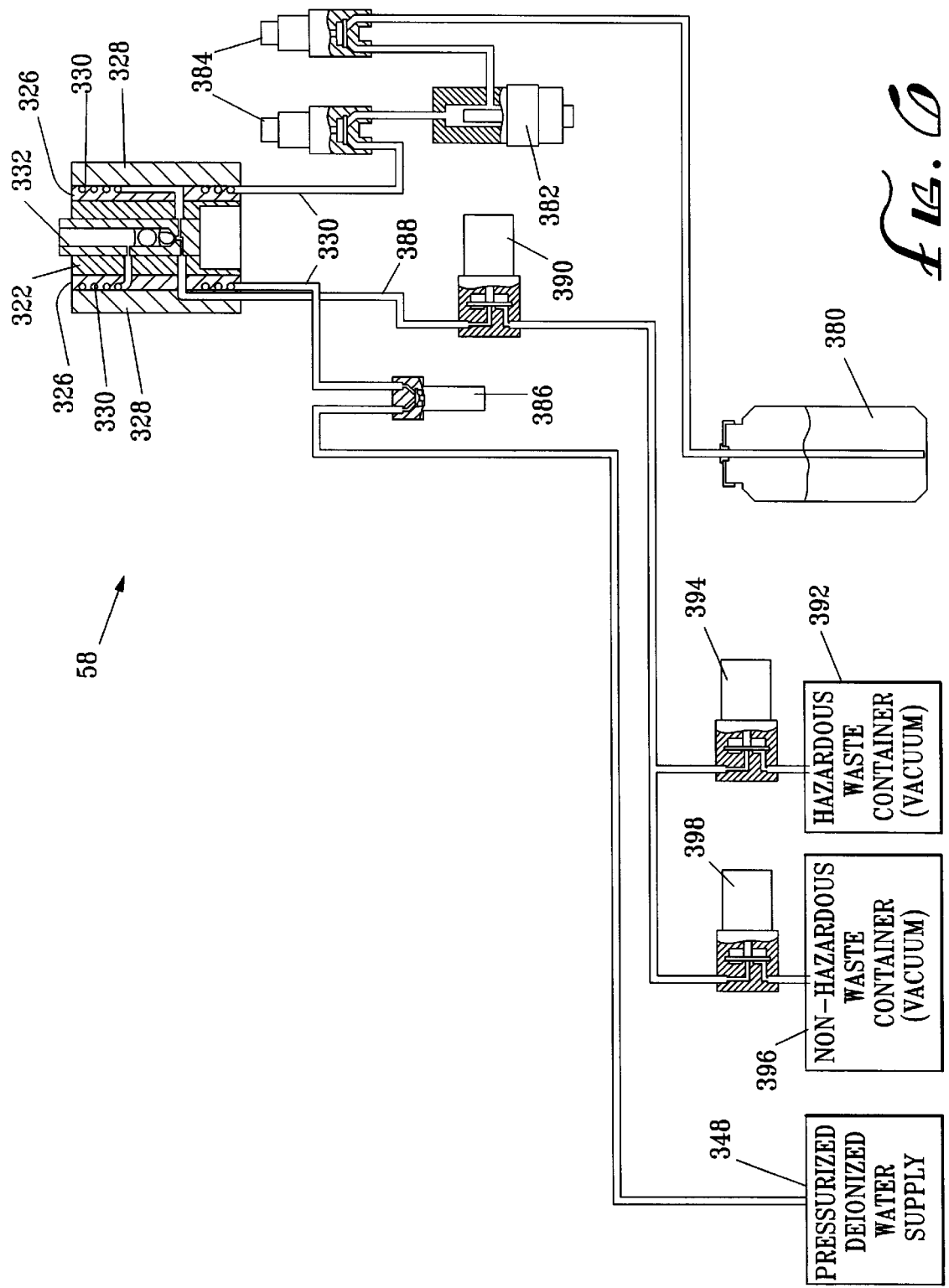
FIG. 6 is a flow diagram showing a reaction cup combination useful in the invention.

FIG. 6 illustrates a flow scheme for a typical reaction cup module. Reagent is provided to a reaction cup 332 via an inlet conduit 330 on one side of the reaction cup module 58 (the right side on FIG. 6). Reagent is pumped from a source of reagent 380 by the reagent pump 59 through remote controllable reagent valves 384 into the inlet conduit 330. Within that portion of the inlet conduit 330 which is partially disposed within the reaction cup module 58, reagent is heated by a heating element 326 before flowing into the reaction cup 332. Deionized rinse water is provided to the reaction cup 332 from a pressurized source of deionized water 348 through a remote controllable deionized water valve 386 and into the inlet conduit 330 on the side of the reaction cup module 58 opposite the inlet conduit 330 through which reagent flows into the reaction cup 332. In that portion of the inlet conduit 330 which is disposed within the reaction cup module 58, deionized rinse water is heated by a second heating element 326 immediately prior to its flow into the reaction cup 332.

The reaction cup 332 is drained via a drain line 388 through a remote controllable master drain valve 390. When the liquid to be drained is of a potentially hazardous sort, the liquid is drained to a suitable hazardous waste container 392 through a remote controllable hazardous waste container valve 394. Where the liquid to be drained is of a non-hazardous sort, the liquid is drained to a suitable non-hazardous waste container 396 through a remote controllable non-hazardous waste container valve 398. Both the hazardous and non-hazardous waste containers 392 and 396 are typically maintained under vacuum to facilitate rapid and complete draining of liquid from the reaction cup 332. Because a separate deionized rinse water source 348 is provided to the reaction cup 332, such deionized rinse water is conveniently and inexpensively used in the rinsing step. Moreover, because water is used in the rinse steps, much of the liquid drained from the reaction cup during the rinsing step can be disposed in a non-hazardous waste disposal area. Note further that because two separate heating elements 326 are used, time lags required for heating are much reduced. This is especially true in analysis operations requiring multiple rinse cycles.

The use of the rinse water system also provides another substantial benefit over the prior art. The analyzing machine 10 using the cup analysis module 58 of the invention can be programmed to periodically and automatically recalibrate a nephelometer used as an analyzer 334, by briefly filling the reaction 332 cup with pure rinse water and calibrating the nephelometer to a predetermined set point. This eliminates having to periodically shut down the machine 10 and manually calibrating each of the nephelometers used in the various reaction cup modules 58.

A particularly useful reaction cup module 58 is disclosed in detail U.S. patent application Ser. No. 08/746,313.

The ion selective electrode analyzing station 22 comprises a sample injection cup 60 disposed in fluid tight communication with a flow cell analyzer 62 capable of measuring at least one electrolyte in a liquid sample. The ion selective electrode analyzing station 22 can be used to simultaneously analyze for sample electrolytes (and sample components which can be analyzed as electrolytes), such as sodium, potassium, calcium, chlorine and carbon dioxide.

Figure 7:
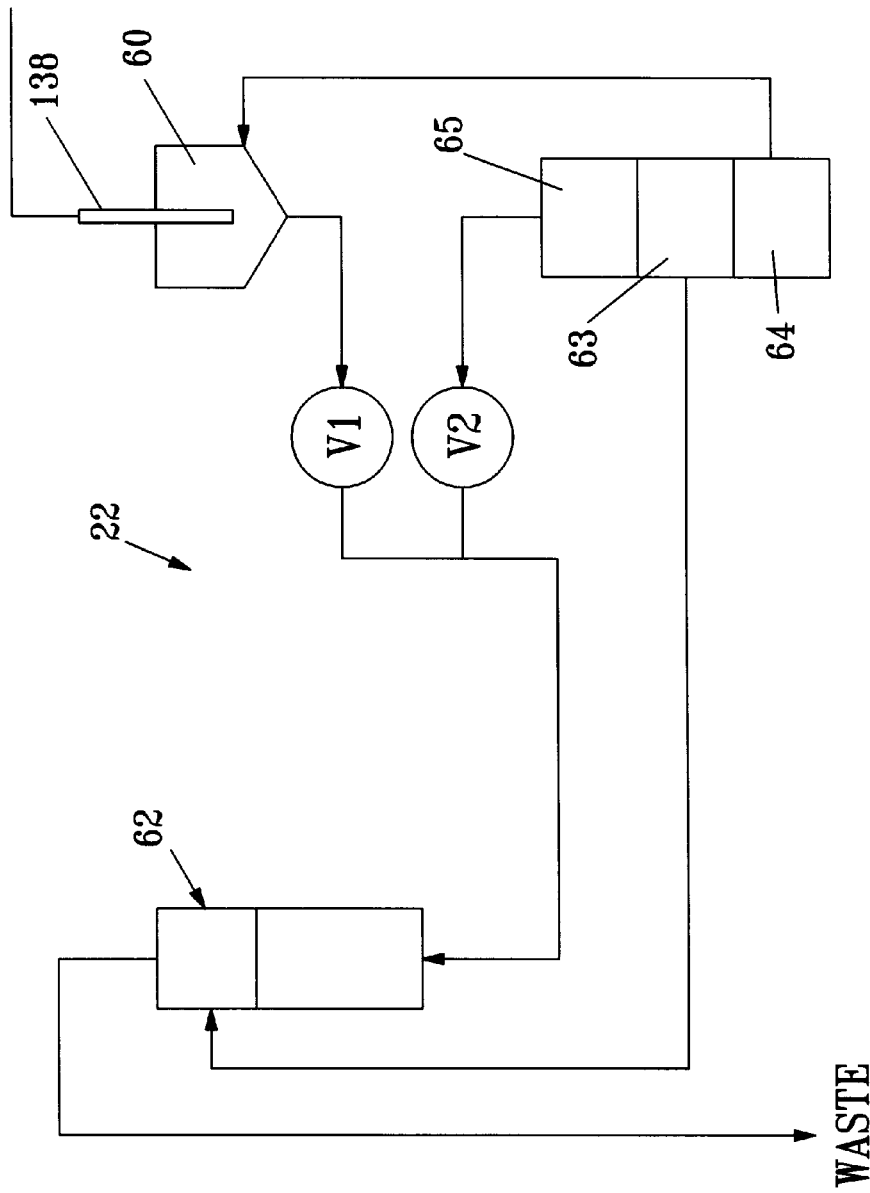
FIG. 7 is a flow diagram showing an ion selective reaction cup assembly useful in the invention.

FIG. 7 illustrates a simplified flow scheme for a typical ion selective analyzing station 22. The sample injection cup 60 is disposed in fluid tight communication with an ion selective electrode analyzing station pump 64 capable of pumping at least one ion selective electrode analyzing reagent from a source of such reagent (not shown) through the sample injection cup 60, through a valve V1, through the flow cell analyzer 62 and then to a suitable waste disposal site. Sample is pressured into the sample injection cup 60 via a cup analysis probe 138 (described below). In the sample injection cup, the sample is mixed with reagent as the reagent is pumped by pump 64 through the sample injection cup 60 and is carried therewith through valve V1 and into the flow cell analyzer.

A $CO_2$ acid reagent pump 63 capable of pumping $CO_2$ acid reagent directly into the flow cell analyzer 62 is disposed in fluid tight communication with a source of $CO_2$ acid reagent (not shown). Also, an ion selective analyzing station reference solution pump 65 is disposed in fluid tight communication with a source of reference solution (not shown). The ion selective electrode analyzing station reference solution pump 65 is capable of pumping reference solution through valve V2 directly into the flow cell analyzer 62.

In a preferred embodiment, the ion selective electrode analyzing station pump 64, the $CO_2$ acid reagent pump 63 and the ion selective electrode analyzing station reference solution pump 65 are driven by a single motor.

A particularly useful ion selective analyzing station 22 is disclosed in detail in U.S. patent application Ser. No. 08/246,560.

In the embodiment shown in the drawings, the analyzing machine 10 further comprises a sample container loading and preparation assembly 68. The loading and preparation assembly 68 comprises a loading mechanism 70 for loading one or more sample containers from a loading area 72 to the sample station 14 along a loading mechanism path 74. The loading mechanism 70 comprises an on-load tray 76 and an off-load tray 78. In the embodiment shown in FIG. 1, the on-load tray 76 and the off-load tray 78 are sized and dimensioned to retain a plurality of sample container racks 34. The on-load tray 76 has a motorized loading arm 80 for pushing a plurality of sample container racks 34 towards the loading mechanism path 74. The off-load tray 78 has a motorized unloading arm (not shown) for pushing the sample container racks 34 away from the loading mechanism path 74.

The loading mechanism path 74 has a motorized loading path arm 82 which moves a single sample container rack 34 along the loading mechanism path 74 on to and off from the sample station 14. A bar code reader 84 is typically disposed along the loading mechanism path 74. The bar code reader 84 is capable of reading bar coded information disposed on each individual sample container 32 as the sample container 32 moves along the loading mechanism path 74.

In the embodiment shown in FIG. 1, the sample container loading and preparation assembly 68 further comprises a sample container cap piercing mechanism 86 capable of piercing the sample container caps 36 so as to leave the caps 36 open for access by the sample extraction cup analysis probes (described below). Such a cap piercing mechanism 86 is disclosed in detail U.S. patent application Ser. No. 08/746,649.

As illustrated in FIGS. 2 and 3, the sample container cap piercing mechanism 86 can be disposed under a sample cap piercing mechanism cover 88.

Figures 5A, 5B, 5C:
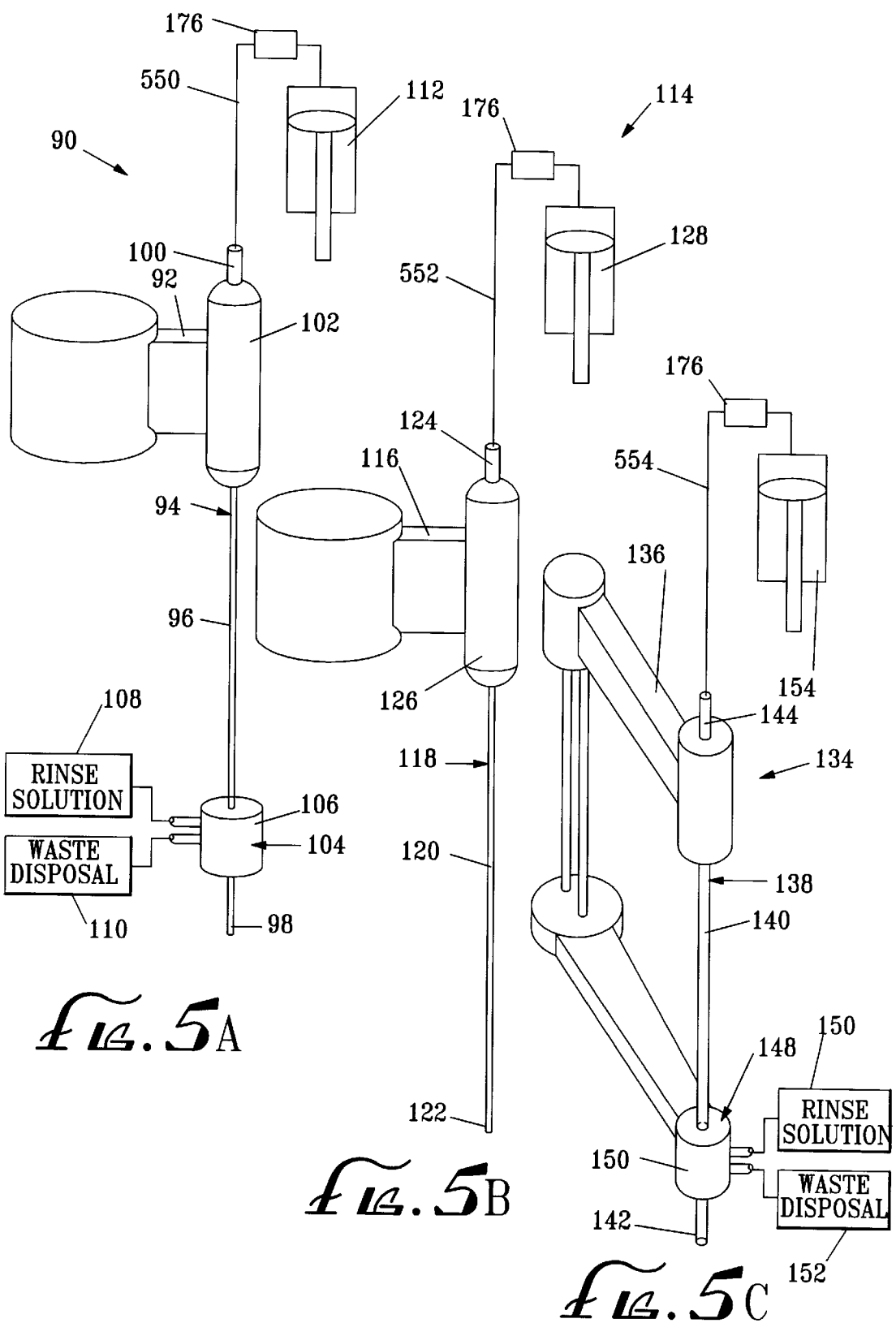
FIG. 5A is a perspective view of a sample probe arm assemble useful in the invention.
FIG. 5B is a perspective view of a reagent probe arm assembly.
FIG. 5C is a perspective view of a cup analyze probe arm assembly.

The analyzing machine 10 further comprises a motorized sample probe arm assembly 90 such as shown in FIG. 5A. The sample probe arm assembly 90 includes a sample probe arm 92 and a hollow sample probe 94. The sample probe 94 has an internal chamber 96, an open lower end 98 and an open upper end 100. The sample probe 94 is disposed generally vertically in the sample probe arm 92 and is movable by a sample probe motor 102 between a lower sample probe position and an upper sample probe position.

The sample probe 94 can be equipped with a sample probe tip cleaning assembly 104 such as is described in U.S. Pat. No. 5,408,891, the entirety of which is incorporated herein by this reference. Such cleaning assembly 104 includes a cleaning assembly chamber 106 connected in fluid tight communication with a source of cleaning liquid 108 and a disposal site 110.

The sample probe arm 92 is movable by a sample probe arm motor (not shown) between a first sample probe arm position wherein the sample probe is immediately above the sample extraction site 38 and a second sample probe arm position wherein the sample probe is immediately above the cuvette sample deposit site 50.

The sample probe 94 is connected to a sample probe pressure altering mechanism capable of alternatively applying a positive pressure and a negative pressure to the internal chamber 96 of the sample probe 94. Such pressure altering mechanism can be any of the various pressure altering mechanisms known in the art. Typically, such pressure altering mechanisms are provided by a syringe pump 112.

The sample probe arm assembly 90 is used to extract a predetermined quantity of sample from sample container 32 disposed within the sample station 14 at the sample extraction site 38 and transport that quantity of sample to a cuvette 44 disposed within the random access analyzing station 18 at the cuvette sample deposit site 50.

The analyzing machine 10 further comprises a motorized reagent probe arm assembly 114 such as shown in FIG. 5B. The reagent probe arm assembly 114 includes a reagent probe arm 116 and a hollow reagent probe 118. The reagent probe 118 has an internal chamber 120, an open lower end 122 and an open upper end 124. The reagent probe 118 is disposed generally vertically in the reagent probe arm 116 and is movable by a reagent probe motor 126 between a lower reagent probe position and an upper reagent probe position.

The reagent probe arm 116 is movable by a reagent probe arm motor (not shown) between a first reagent probe arm position wherein the reagent probe 118 is immediately above the reagent extraction site 42 and a second reagent probe arm position wherein the reagent probe is immediately above the cuvette reagent deposit site 52.

The reagent probe 118 is connected to a reagent probe pressure altering mechanism capable of alternatively applying a positive pressure and a negative pressure to the internal chamber 120 of the reagent probe 118. Such pressure altering mechanism can be any of the various pressure altering mechanisms known in the art. Typically, such pressure altering mechanisms are provided by a syringe pump 128.

The reagent probe arm 116 is used to extract a predetermined quantity of reagent from a reagent container 40 disposed within the reagent station 16 at the reagent extraction site 42 and transport that quantity of reagent to a cuvette 44 disposed within the random access analyzing station 18 at the cuvette reagent deposit site 52.

Both the sample probe arm 92 and the reagent probe arm 116 can include multiple independently movable probes. In the embodiment illustrated in the drawings, both the sample probe arm 92 and the reagent probe arm 116 comprise a pair of probes each independently movable about a primary axis of rotation 130. Both probe arms are also rotatable as a whole about a secondary axis of rotation 132.

The analyzing machine 10 further comprises a cup analysis probe arm assembly 134 such as shown in FIG. 5C. The cup analysis probe arm assembly 134 includes a cup analysis probe arm 136 and a hollow cup analysis probe 138. The cup analysis probe 138 has an internal chamber 140, a lower end 142 and an open upper end 144. The cup analysis probe 138 is disposed generally vertically in the cup analysis probe arm 136 and is movable by a cup analysis probe motor (not shown) between a lower cup analysis probe position and an upper analysis probe position.

The cup analysis probe 138 can be equipped with a cup analysis probe tip cleaning assembly 146 such as is known in the prior art. Such cleaning assembly includes a cleaning assembly chamber 148 connected in fluid tight communication with a source of cleaning liquid 150 and a disposal site 152.

The cup analysis probe arm 136 is movable by a cup analysis probe arm motor (not shown) between a first cup analysis probe arm position wherein the cup analysis probe is immediately above a sample container 32 in the sample station 14, a second cup analysis probe arm position wherein the cup analysis probe 136 is immediately above one of the reaction cup modules 58 and a third cup analysis probe arm position wherein the cup analysis probe 136 is immediately above the sample injection cup 60.

The cup analysis probe 136 is connected to a cup analysis probe pressure altering mechanism capable of alternatively applying a positive pressure and a negative pressure to the internal chamber 140 of the cup analysis probe 136. Such pressure altering mechanism can be any of the various pressure altering mechanisms known in the art. Typically, such pressure altering mechanisms are provided by a syringe pump 154.

The cup analysis probe arm assembly 134 is used to extract a predetermined quantity of sample from a sample container 32 disposed within the sample station 14 and transport that quantity to each of the reaction cup modules 58 and to the sample injection cup 60.

The analyzing machine 10 further comprises a cuvette stirring rod assembly 156 such as shown in FIG. 5D. The cuvette stirring rod arm assembly 156 includes an elongate rotatable cuvette stirring rod 158 having a lower end 160 and an upper end 162. The lower end 160 of the cuvette stirring rod includes a cuvette stirring rod paddle 164 attached thereto. The cuvette stirring rod is generally disposed vertically and is movable between a lower cuvette stirring rod position and an upper stirring rod position. The cuvette stirring rod arm assembly 156 is positionable above the cuvette mixing site 54. As illustrated by the embodiments shown in the drawings, the motorized cuvette stirring rod assembly 156 can be an independent and separate assembly or it can be integrated with the sample probe arm 92 and/or the reagent probe arm 116.

The analyzing machine 10 further comprises a cuvette wash station 166 as shown in FIG. 5E. The cuvette wash station probe 168 is used to extract liquid reaction mixtures from the cuvettes 44, dispose such mixtures to a suitable disposal site and then rinse and clean the cuvette 44 so that it can be used to analyze another quantity of sample.

The wash station 166 comprises one or more motorized cuvette wash station probes 168. Each wash station probe 168 has an internal chamber 170, an open lower end 172 and an open upper end 174. The wash station probe 168 is disposed generally vertically above the cuvette washing site 56 in the random access analyzing station 18 and is movable by a wash station probe motor (not shown) between a lower wash station probe position and an upper wash station probe position.

In the embodiment shown in the drawings, the wash station probes 168 operated in pairs, one of each pair of wash station probes 168 being connected to a source of pressurized rinse solution and the other wash station probe 168 of each pair being connected to a disposal system adapted to vacuum out the contents of a cuvette and transfer such contents to a suitable disposal site.

Alternatively, each individual wash station probe 168 can be connected to a wash station probe pressure altering mechanism capable of alternatively applying a positive pressure and a negative pressure to the internal chamber 170 of the wash station probe 168. The wash station probe pressure altering mechanism includes a mechanism for providing pressurized washing liquid from a source of washing liquid to the wash station probe 168 for washing a cuvette disposed at the cuvette washing site 56 and a mechanism for providing a negative pressure to the interior chamber 170 of the wash station probe 168 for removing waste liquids from a cuvette disposed at the cuvette washing site 56 and for transferring such waste liquids to a disposal site.

Such a mechanism for providing negative pressure to the interior chamber 170 typically comprises a source of vacuum.

Each of the pressure altering mechanisms usable in the analyzing machine can further comprise an obstruction detector 176 comprising a pressure detector 502 operatively installed within the operative pressure transmitting conduits to alert the operator and/or shut down the machine should an obstructive pressure drop be detected within the pressure altering mechanism.

In one preferred embodiment, the obstruction detector 176 comprises a housing 504 and a first conduit 506, a second conduit 508 and the pressure detector 502 disposed within the housing 504. The first conduit 506 has an open inlet 512 end and an outlet end 514. The second conduit 508 has an inlet end 516 disposed in fluid tight communication with the outlet end 514 of the first conduit 506 and an open outlet end 518.

The pressure detector 502 is disposed within the housing 504 in abutment with the outlet end 514 of the first conduit 506 and the inlet end 516 of the second conduit 508, such that the pressure detector 502 is in direct operative contact with the fluid flowing within the first and second conduits 506 and 508. As noted above, the term "direct operative contact" means that the pressure detector 502 contacts the fluid flowing within the conduits 506 and 508 without use of any intermediary nonflowing fluid-filled conduit. Preferably, the pressure detector 502 is a pressure transducer having a pressure sensitive surface 520.

In those embodiments wherein the pressure detector 502 is a pressure transducer having a pressure sensitive surface 520 disposed within a transducer plane 522, it is further preferable that the first conduit 506 is linear and is disposed at an angle $\alpha$ with respect to the transducer plane 522 of between about 50° and about 75°, most preferably between about 65° and about 70°. Likewise, in such embodiments wherein the pressure detector 502 is a pressure transducer having a pressure sensitive surface 520, it is additionally preferred that the second conduit 508 is linear and is disposed at an angle $\beta$ with respect to the transducer plane 522 of between about 50° and about 75°, most preferably between about 65° and about 70°.

Also, it is preferable that the first conduit 506 and the second conduit 508 are disposed within a single conduit plane.

Typically, the housing 504 is made from a lightweight molded material, such as a thermal plastic. Acrylics have been found suitable as materials for the housing 504.

Figure 8:
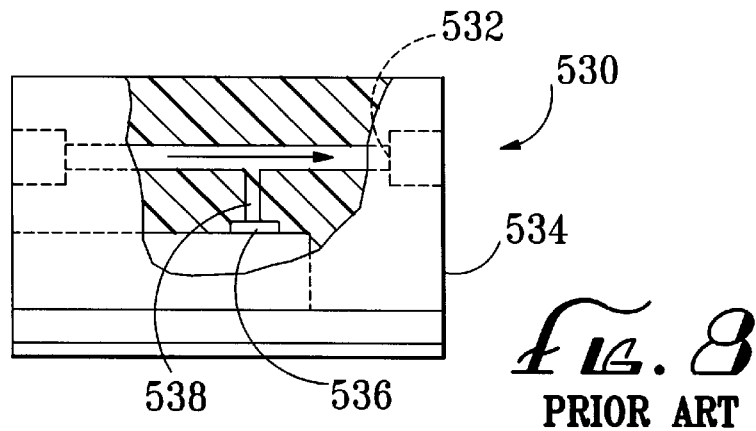
FIG. 8 is a cross-sectional side view of a fluid pressure detecting device of the prior art.
Figure 9:
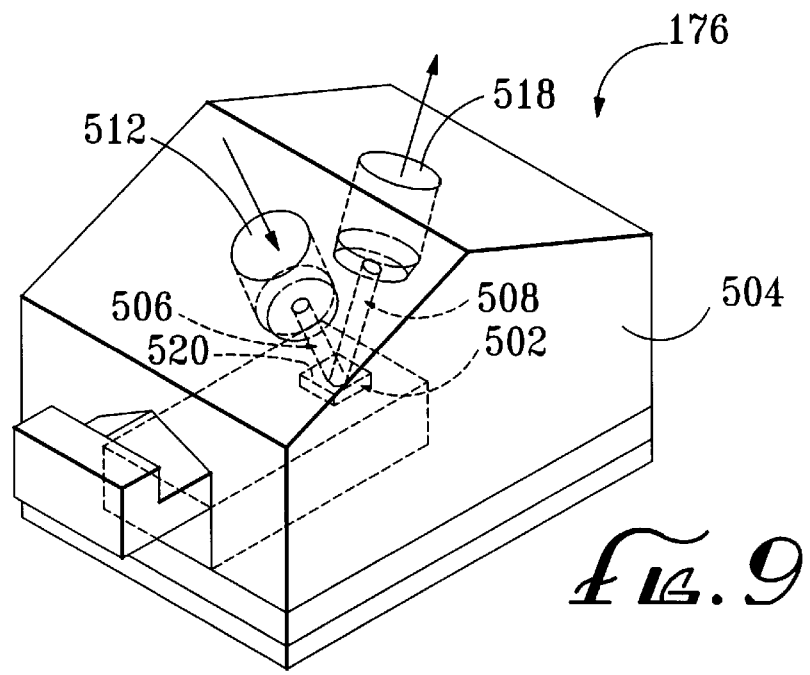
FIG. 9 is a perspective view of a fluid pressure detecting device having features of the invention.
Figure 10:
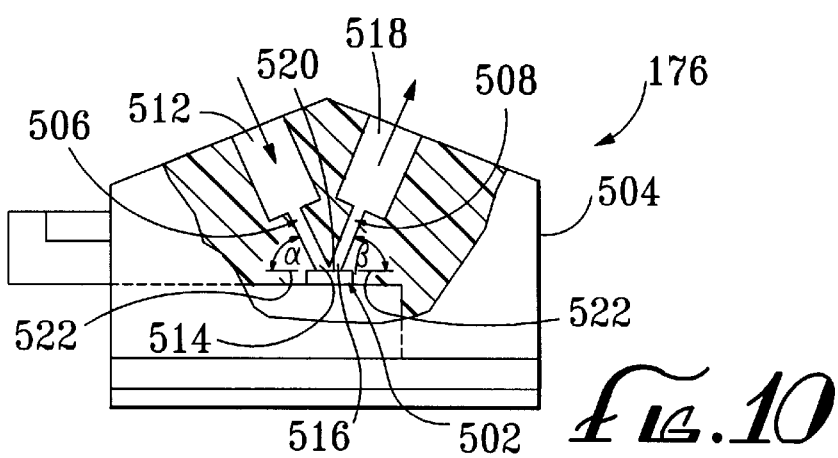
FIG. 10 is a cross-sectional side view of the fluid pressure detecting device illustrated in FIG. 9.

The configuration of the obstruction detector 176 of the invention is contrasted with prior art obstruction detectors 530 as shown in FIG. 8. Such prior art obstruction detectors 530 comprised a single conduit 532 disposed within a housing 534. Also disposed within the housing 534 is a pressure detector 536, such as a pressure transducer.

A principal difference between the obstruction detector 176 of the invention and such obstruction detectors 530 of the prior art is that, in the obstruction detectors 530 of the prior art, the pressure of the fluids flowing within the linear conduit 532 is transmitted to the pressure detector 536 via an intermediary conduit 538 which is typically filled with a fluid such as 6–10 microliters of air or carrier liquid. Unfortunately, such intermediary conduits 538 tend to delay and dampen pressure transmissions from carrier fluids flowing within the linear conduit 532 to the pressure detector 536. Also, because the intermediary conduits 538 do not have fluids flowing through them, they tend to become clogged with foreign material. The invention eliminates these problems in the prior art by eliminating the use of an intermediary conduit 538.

In the obstruction detector 176 of the invention, it is further preferable to use as a carrier fluid flowing within the pressure transmitting conduits 506 and 508 a degassed liquid, such as water degassed under at least about 20 inches of mercury. By degassing the carrier liquid, pressures transmitted to the pressure detector 502 are less delayed and dampened than they are in prior art systems containing non-degassed carrier fluids.

In operation, the obstruction detector 176 is mounted within the carrier fluid lines connecting the aspiration/ejection probe to the pressure altering mechanism. Such an installation is shown, for example, in FIGS. 5A, 5B and 5C, wherein the obstruction detector 176 is disposed within the carrier fluid lines 550, 552 and 554, respectively. The carrier fluid within each carrier fluid line 550, 552 and 554 flows through the obstruction detector 176 via openings 512 and 518. As the carrier fluid contacts the pressure sensitive surface 520, the pressure detector 502 monitors the pressure of the carrier fluid. When the carrier fluid pressure is detected to be below a pre-set minimum, the pressure detector 502 sends a signal to the controller 178 (described below), essentially alerting the controller that a potential obstruction has occurred within the carrier fluid line 550, 552 or 554.

Typically, the automated analyzing machine 10 further comprises a controller 178 for controlling each of the various motors in a way which provides for the smooth, efficient and rapid operation of the machine 10. The control is typically also used to retain and report analysis data. Preferably, the controller 178 comprises a digital computer which can be preprogrammed with a large variety of operating instructions depending upon the samples being analyzed, the analyses to be run and the reagents at hand. Most preferably, the digital computer receives bar coded information regarding each of the samples to be analyzed, and the reagents in the reagent station 16 and uses that information to most efficiently conduct the analyses. Also, it is preferable that the controller 178 keep track of the amounts of reagents used so as to alert the operator whenever reagent in any particular reagent container 40 begins to run low.

Also, it is preferable that the controller 178 include a "stat" mode, which gives the operator the ability to require the machine 10 to analyze particularly important samples in the reaction cup and ion selective electrode analyzing stations ahead of all other samples.

In operation, the operator of the automated analyzing machine of the invention 10 places samples to be analyzed in individual sample containers 32 and places each sample container 32 in one or more sample container racks 34. The sample container racks 34 are placed in the on-load tray 76.

The motorized loading arm 80 pushes sample container racks 34 in the on-load tray 76 towards the loading mechanism path 74. As each sample container rack 34 enters the loading mechanism path 74, the motorized loading path arm 82 pushes the sample container rack 34 along the loading mechanism path 74 towards the sample station 14.

As the sample containers 32 pass by the bar code reader 84, bar-coded information appended to each sample container 32 is read by the bar code reader 84 and is transmitted to the controller 178. Such bar code coded information typically includes the identity of the sample and the analyses which are to be run using individual portions of the sample.

As the sample container rack 34 is pushed further along the loading mechanism path 74, it passes under the cap piercing mechanism 86. The cap piercing mechanism 86 pierces the caps 36 on each of the sample containers 32.

The sample container rack 34 then is loaded into the sample station 14 wherein a clamping mechanism within the sample station 14 holds the sample container rack 34 firmly upright.

The sample station 14 is rotated under the control of the controller 178. When an individual sample container 32 is placed at a sample extraction site 38, a small quantity of the sample is extracted from the sample container 32 by the sample probe 94. This is accomplished by positioning the sample probe 94 above the sample extraction site 38, lowering the sample probe 94 to the lower sample probe position wherein the open-ended lower end 98 of the sample probe 94 is placed below the surface of the sample within the sample container 32. A small quantity of the sample is then extracted into the sample probe internal chamber 96 by drawing a vacuum on the sample probe internal chamber 96 using the sample probe pressure altering mechanism. The sample probe 94 is then raised to the upper sample probe position and the sample probe arm 92 moves the sample probe 94 to a position where it is directly above the cuvette sample deposit site 50.

At the cuvette sample deposit site 50, the sample probe 94 is again lowered to the lower sample probe position and the quantity of sample within the sample probe 94 is deposited into a cuvette 44 positioned at the cuvette sample deposit site 50. This is done by creating a slight elevated pressure within the sample probe internal chamber 96 using the sample probe pressure altering mechanism. The lower end of the sample probe 94 is then retracted into the sample probe tip cleaning assembly 104 where it is rinsed using cleaning liquid from the source of cleaning liquid 108. After cleaning, the cleaning liquid is flushed to a suitable disposal site 110. The sample probe 94 is then ready to extract another quantity of sample from another sample container 32.

Contemporaneously with the above-described action of the sample probe 94, the reagent probe 118 is used in similar fashion to extract a quantity of an appropriate pre-mixed reagent from the reagent station 16 and depositing that quantity of reagent into the cuvette 44. Usually the reagent is added to the cuvette immediately prior to the deposit of the sample within the cuvette 44.

After sample and reagent are both added to the cuvette 44, the cuvette 44 is rotated to the cuvette mixing site 54. At the cuvette mixing site 54, the cuvette stirring rod 158 is lowered to the lower cuvette stirring rod position and the stirring rod paddle 164 is rotated so as to agitate and thoroughly mix the sample and reagent within the cuvette 44.

In typical random access analyzing operations wherein analyses are carried out at an elevated temperature, the mixture of sample and reagent within the cuvette 44 is then allowed to stand within the random access analyzing station 18 while the mixture is brought up to temperature, such as by blowing heated air through the random access analyzing station 18. When the mixture within the cuvette 44 has reached proper temperature, the contents of the cuvette 44 are analyzed using the random access analyzing station analyzer 46. In a preferred operation, the cuvette 44 is placed at the random access analyzing station analyzing site 46 a plurality of times and is thereby analyzed a plurality of times so that the reportable results are derived from an average of the plurality of analyses. The reportable results are thereby extremely reliable.

After analyses are completed regarding the mixture within the cuvette 44, the cuvette 44 is moved to the cuvette washing site 56 at the cuvette wash station 166. At the cuvette wash station 166, a wash station probe 168 is moved from its upper probe position to the lower probe position and the reaction mixture is extracted using the wash station pressure altering mechanism. Depending upon the kind of mixture which had been analyzed within the cuvette 44, the cuvette 44 is then rinsed once or several times using pressurized washing liquid. After the rinse liquid is removed from the cuvette 44 and sent to suitable disposal, the cuvette 44 is ready to accept another sample for analysis.

Contemporaneously with the operation of the random access analyzing station 18, high volume analyses are performed in the reaction cup analyzing station 20 and in the ion selective electrode analyzing station 22. First, a predetermined quantity of an appropriate reagent is pumped into each reaction cup 332 and into the injection sample cup 60 using the reagent pump 59. The magnetic stirrer is engaged. Then, the cup analysis probe arm assembly 134 positions the cup analysis probe 136 above a sample container 32 within the sample station 14, the cup analysis probe 136 is lowered to the lower probe position and a relatively large quantity of sample is extracted into the internal chamber 140 within the cup analysis probe 138 using the cup analysis probe pressure altering mechanism. The cup analysis probe 138 is then raised to the upper probe position and the cup analysis probe arm 136 moves the cup analysis probe 138 to a position directly above one of the reaction cup modules 58. The cup analysis probe 138 is lowered to the lower cup position and a portion of the sample within the cup analysis probe 138 is deposited within the reaction cup 332. The cup analysis probe 138 is then again raised to the upper probe position and the cup analysis probe arm 136 moves the cup analysis probe 138 to immediately above each of the other reaction cup modules 58 and deposits a portion of the sample within each such reaction cups 332.

When all of the reaction cups 332 are filled, the cup analysis probe arm 136 moves the cup analysis probe 138 to directly above the sample injection cup 60. The cup analysis probe 138 is again lowered to the lower probe position and the remainder of the sample is deposited within the injection sample cup 60.

After the mixture of reagent and sample is thoroughly mixed by the magnetic stirrer, the mixture is analyzed using the reaction cup analyzing station analyzer 334 in each cup module, and the results of the analyses are reported to the controller 178. The reaction cups 332 are then rinsed and ready for another sample.

Contemporaneously, in the ion specific electrode analysis station, the quantity of sample within the injection sample cup 60 is thoroughly flow mixed with the reagent. After the sample and reagent are properly mixed, the mixture is passed through the flow cell 62 where individual electrodes within the flow cell 62 each perform a single analysis on the mixture. The results of the analysis are reported to the controller 178. The mixture is then drained to a suitable disposal site 66 and the system is rinsed in preparation for the analysis of another sample.

After the sample within each of the sample containers 32 in a sample container rack 34 are analyzed, the sample container rack 34 is removed from the sample station 14 using the motorized loading path arm 82. The sample container rack 34 is retracted along the loading mechanism path 74 to the off-load tray 78. Once in the off-load tray 78, the motorized unloading arm pushes the sample container rack 34 towards the end of the off-load tray 78 where it is removed by the operator.

The invention provides significant improvements over the prior art by reducing throughput times, maintenance costs and operating expense, while increasing accuracy and reliability.

Although the present invention has been described in considerable detail with reference to certain preferred versions thereof, other versions are possible. Therefore, the spirit and scope of the appended claims should not be limited to the description of the preferred versions contained herein.

What is claimed is:

1. A device for detecting the pressure of a fluid, the device comprising:

(a) a housing;

(b) a first conduit disposed within the housing, the first conduit having an open inlet end and an outlet end;

(c) a second conduit disposed within the housing, the second conduit having an inlet end butting and in fluid tight communication with the outlet end of the first conduit and an open outlet end; and (d) a pressure detector disposed within the housing in abutment with the outlet end of the first conduit and with the inlet end of the second conduit such that the pressure detector is in direct operative contact with a fluid flowing within the first and second conduits;

wherein the first conduit and the second conduit are disposed within a single conduit plane at an angle with respect to one another of less than 180°.

2. The device of claim 1 wherein the pressure detector is a pressure transducer having a pressure sensitive surface.

3. The device of claim 2 wherein the pressure sensitive surface of the transducer is disposed within the body tangent to a transducer plane and wherein the first conduit is linear and is disposed at an angle with respect to the transducer plane of between about 50° and about 75°.

4. The device of claim 3 wherein the first conduit is disposed at an angle with respect to the transducer plane of between about 65° and about 70°.

5. The device of claim 2 wherein the pressure sensitive surface of the transducer is disposed within the body tangent to a transducer plane and wherein the second conduit is linear and is disposed at an angle with respect to the transducer plane of between about 50° and about 75°.

6. The device of claim 5 wherein the second conduit is disposed at an angle with respect to the transducer plane of between about 65° and about 70°.

7. The device of claim 2 wherein the pressure sensitive surface of the transducer is disposed within the body tangent to a transducer plane, wherein the first conduit is linear and is disposed at an angle with respect to the transducer plane of between about 50° and 75° and wherein the second conduit is linear and is disposed at an angle with respect to the transducer plane of between about 50° and about 75°.

8. The device of claim 7 wherein the first conduit is disposed at an angle with respect to the transducer plane of between about 65° and about 70° and wherein the second conduit is disposed at an angle with respect to the transducer plane of between about 65° and about 70°.

* * * * *